United States Patent
Davis et al.

(10) Patent No.: US 9,009,897 B2
(45) Date of Patent: Apr. 21, 2015

(54) PILLOW AND METHOD FOR USE WITH ASSISTED BREATHING MASKS

(75) Inventors: Edmund Scott Davis, Ft. Lauderdale, FL (US); Antonio Arcieri, Ft. Lauderdale, FL (US)

(73) Assignee: Banyan Licensing L.L.C., Charlotte, NC (US)

( * ) Notice: Subject to any disclaimer, the term of this patent is extended or adjusted under 35 U.S.C. 154(b) by 803 days.

(21) Appl. No.: 12/016,544

(22) Filed: Jan. 18, 2008

(65) Prior Publication Data

US 2009/0139031 A1    Jun. 4, 2009

Related U.S. Application Data (60) Provisional application No. 60/885,806, filed on Jan. 19, 2007.

(51) Int. Cl.
| A47G 9/10 | (2006.01) |
| A61G 7/07 | (2006.01) |
| A61G 13/12 | (2006.01) |
| A61M 16/06 | (2006.01) |

(52) U.S. Cl.
CPC *A47G 9/10* (2013.01); *A61G 7/072* (2013.01); *A61G 13/121* (2013.01); *A61G 2200/322* (2013.01); *A61M 16/06* (2013.01); *A61M 16/0683* (2013.01); *A61M 16/0633* (2014.02)

(58) Field of Classification Search
USPC .......................... 5/636, 638, 645, 490; D6/601
See application file for complete search history.

(56) References Cited

U.S. PATENT DOCUMENTS

| 3,638,251 | A | * | 2/1972 | Weiss | 5/485 |
| 3,667,074 | A | * | 6/1972 | Emery | 5/636 |
| 4,349,925 | A | * | 9/1982 | Macomber | 5/632 |
| 4,752,064 | A | * | 6/1988 | Voss | 5/638 |
| 5,018,231 | A | * | 5/1991 | Wang | 5/636 |
| 5,163,194 | A |   | 11/1992 | Dixon |  |
| 5,269,035 | A | * | 12/1993 | Hartunian | 5/638 |
| 5,613,501 | A | * | 3/1997 | Michelson | 5/637 |
| D445,505  | S | * | 7/2001 | Shapiro | D24/183 |

(Continued)

FOREIGN PATENT DOCUMENTS

WO    WO 01/24668    4/2001

OTHER PUBLICATIONS

The International Search Report for PCT Application No. PCT/US2008/051459; Filed Jan. 18, 2008; Date of Completion Jun. 4, 2008; Date of Mailing Jun. 13, 2008.

(Continued)

*Primary Examiner* — Robert G Santos
(74) *Attorney, Agent, or Firm* — Moore & Van Allen PLLC (57) ABSTRACT

A device for use with a respiratory mask comprises a pillow having at least one recess structured to receive the mask so that the pillow does not exert substantial pressure on the mask, and a cover that at least partially covers the exterior surface of the pillow and substantially follows the contours of the at least one recess. A method of using a respiratory mask comprises providing a pillow having at least one recess, positioning a cover on the pillow so that the cover substantially follows the contours of the at least one recess, positioning a respiratory mask on the head of a user, and positioning the user's head on the cover and pillow such that the mask is received in the at least one recess so that the pillow and cover do not exert substantial pressure on the mask.

17 Claims, 12 Drawing Sheets

(56) References Cited

U.S. PATENT DOCUMENTS

| | | | |
|---|---|---|---|
| 6,427,272 B1 * | 8/2002 | Yacoub | 5/638 |
| D474,364 S | 5/2003 | Arcieri | |
| 6,574,809 B1 | 6/2003 | Rathbun | |
| 6,622,325 B1 | 9/2003 | Garza | |
| 6,629,324 B1 * | 10/2003 | Shapiro | 5/636 |
| 6,745,772 B1 | 6/2004 | McLeod | |
| 6,842,924 B1 * | 1/2005 | Walters | 5/637 |
| 6,913,019 B2 * | 7/2005 | Johns et al. | 128/845 |
| 6,915,539 B2 | 7/2005 | Rathbun | |
| 7,063,085 B2 * | 6/2006 | Silva et al. | 128/202.18 |
| 7,082,633 B1 | 8/2006 | Maarbjerg | |
| D529,325 S * | 10/2006 | Maarbjerg | D6/601 |
| D558,499 S * | 1/2008 | Maarbjerg | D6/601 |
| D595,530 S * | 7/2009 | Deetsch | D6/601 |
| D595,531 S * | 7/2009 | Deetsch | D6/601 |
| 7,607,433 B2 * | 10/2009 | Silva et al. | 128/201.24 |
| 2003/0188385 A1 * | 10/2003 | Rathbun | 5/636 |
| 2003/0217412 A1 | 11/2003 | Johns et al. | |
| 2006/0037608 A1 * | 2/2006 | Silva et al. | 128/202.18 |
| 2006/0130844 A1 | 6/2006 | Ho et al. | |
| 2006/0278219 A1 * | 12/2006 | Silva et al. | 128/202.18 |
| 2009/0139031 A1 * | 6/2009 | Davis et al. | 5/639 |

OTHER PUBLICATIONS

The Written Opinion for PCT Application No. PCT/US2008/051459; Filed Jan. 18, 2008; Date of Completion Jun. 4, 2008; Date of Mailing Jun. 13, 2008.

* cited by examiner

PILLOW AND METHOD FOR USE WITH ASSISTED BREATHING MASKS

CROSS-REFERENCE TO RELATED APPLICATION

The present application claims the benefit of the filing date of U.S. Provisional Patent Application Ser. No. 60/885,806 filed on Jan. 19, 2007, the entire disclosure of which is incorporated herein by reference.

FIELD OF THE INVENTION

The present invention relates to a pillow for use with assisted breathing masks to facilitate resting and sleep.

BACKGROUND OF THE INVENTION

Users of respiratory masks often have difficulty resting or sleeping because pressure on the mask exerted by a pillow while side sleeping can impede the performance and comfort of the mask, cause the mask seal to separate from the face and result in air leakage (which can cause irritation from the eyes drying out), and/or cause the mask to press uncomfortably against the user's face. Users of respiratory masks often try to compensate for leaks and positional problems by tightening the mask against the face more than otherwise required, causing further discomfort. The ultimate effect of these problems is sleep interruption or non-compliance by the user (i.e., the user stops using the mask).

BRIEF SUMMARY OF THE DISCLOSURE

The present disclosure relates to a device and method for assisting users of respiratory masks to rest and sleep while wearing and using the mask. The device and method enable the user to sleep in multiple positions while minimizing pressure exerted on the face by the mask. In accordance with one aspect of the invention, a device for use with a respiratory mask comprises a pillow having a head-supporting upper surface defining at least one recess structured to receive the mask when the user is in a side-lying position so as to substantially prevent pressure from being exerted on the mask by the pillow, and a cover that at least partially covers the exterior surface of the pillow and substantially follows (i.e., conforms to) the contours of the at least one recess.

In accordance with another aspect of the invention, a method of using a respiratory mask comprises providing a pillow having a head-supporting upper surface that defines at least one recess configured to receive the mask when a user is in a side-lying position, positioning a respiratory mask on the head of a user, and positioning the user's head on the cover and pillow such that the mask is received in the at least one recess so that the pillow and cover do not exert substantial pressure on the mask.

The cover in some embodiments comprises a plurality of separate fabric pieces sewn together. In one preferred embodiment, one fabric pieces covers a majority of the upper surface of the pillow, and separate fabric pieces cover the at least one recess.

BRIEF DESCRIPTION OF THE SEVERAL VIEWS OF THE DRAWING(S)

Reference will now be made to the accompanying drawings, which are not necessarily drawn to scale, and wherein.

DETAILED DESCRIPTION OF THE DRAWINGS

Figure 1:
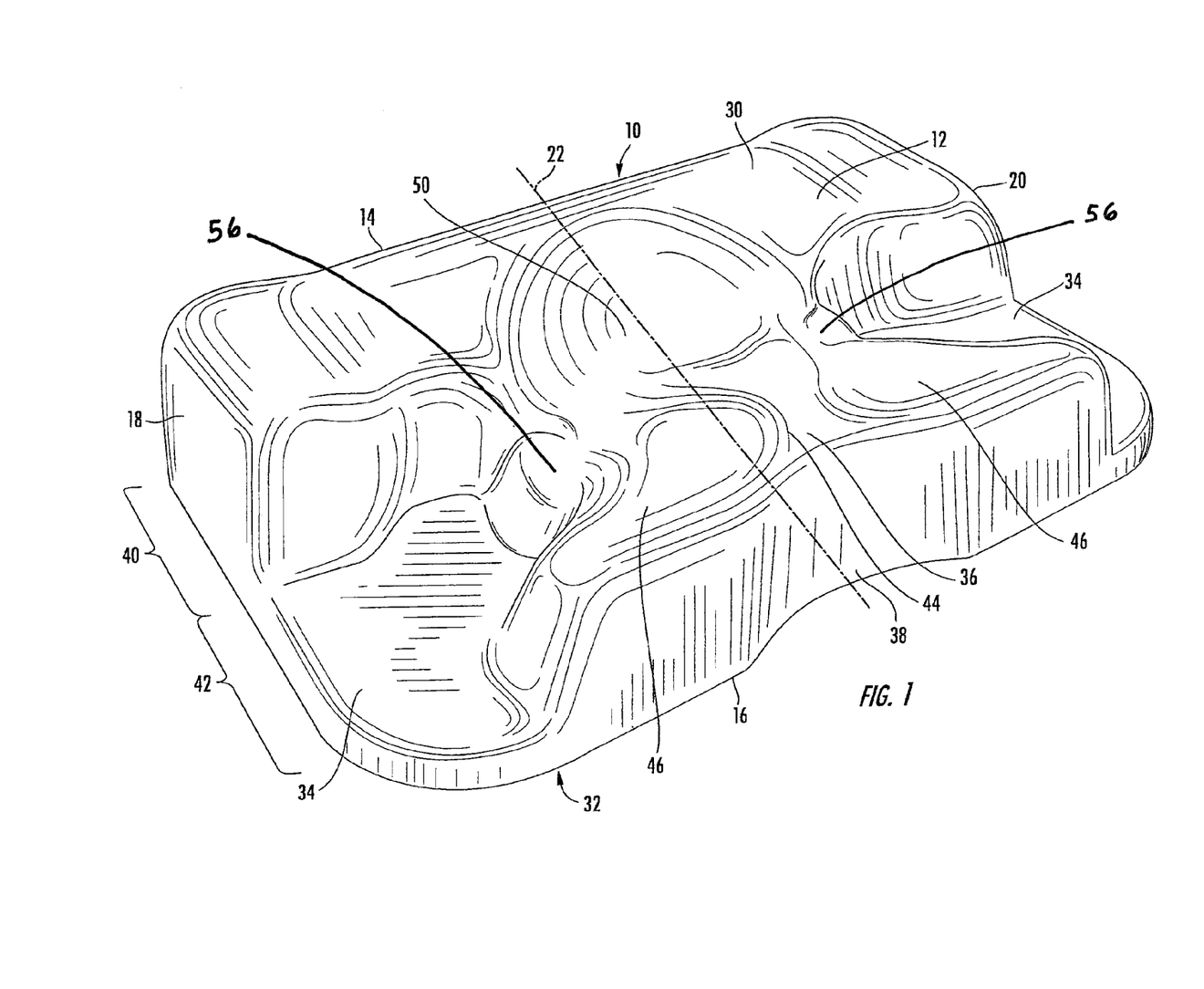
FIG. 1 is a perspective view of the pillow, according to one embodiment of the invention.
Figure 7:
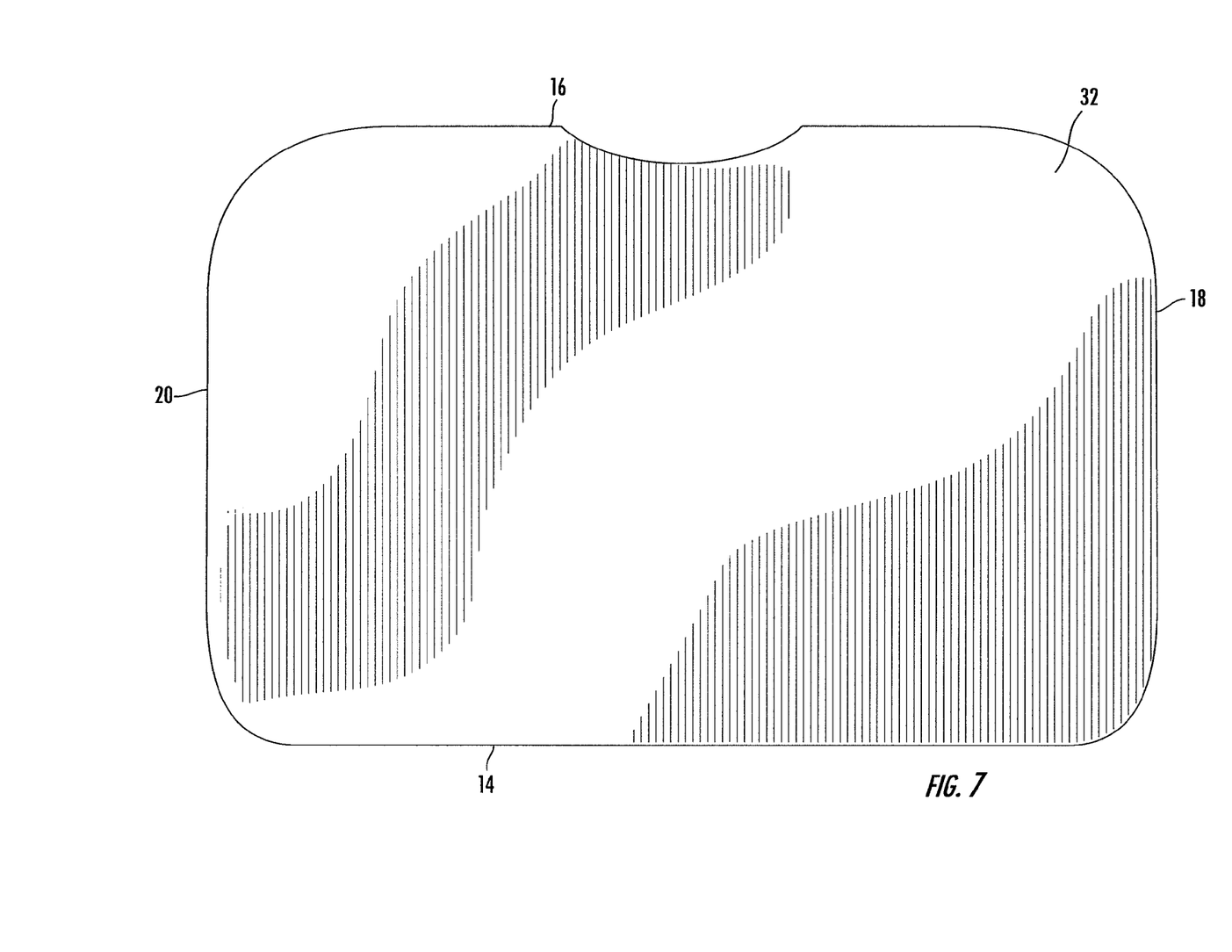
FIG. 7 is a bottom plan view illustrating the pillow of FIG. 1.
Figure 8:
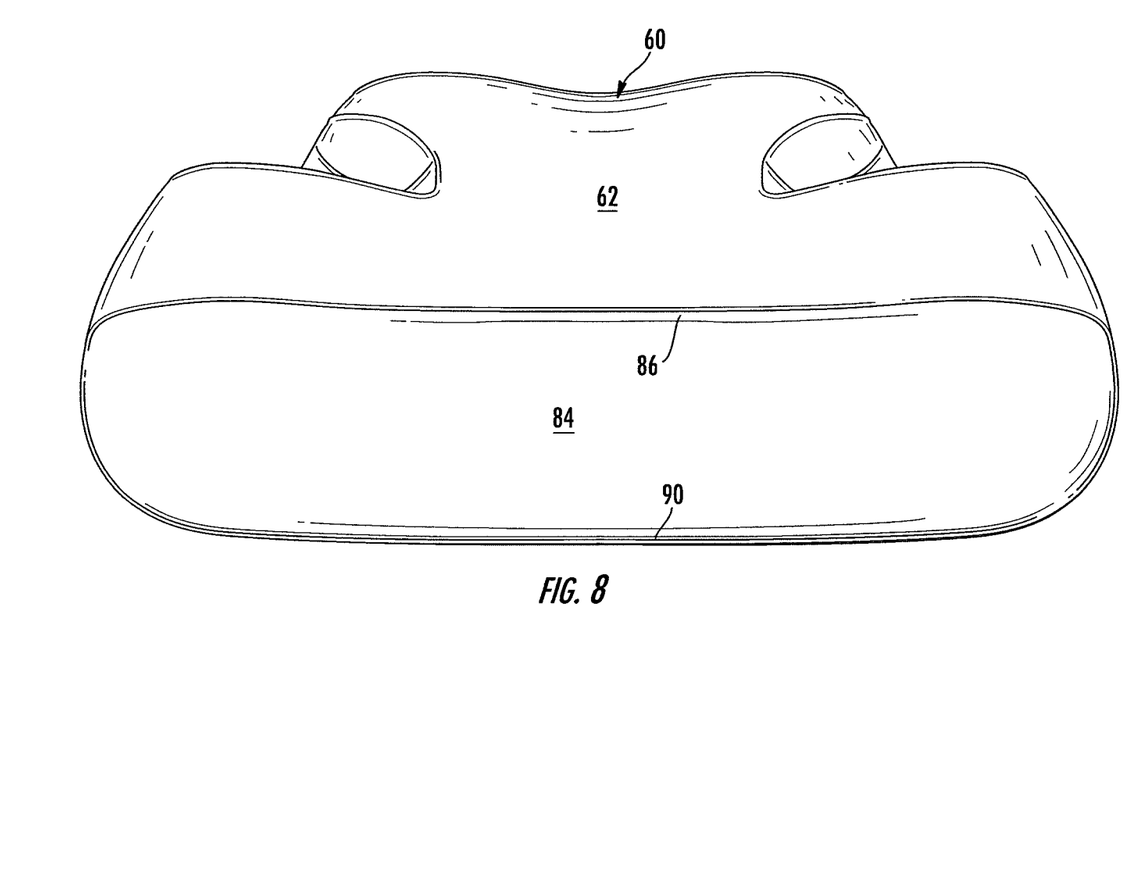
FIG. 8 is a rear view illustrating the cover for the pillow of FIG. 1.

Referring to the drawings and in particular FIG. 1, there is illustrated a pillow 10 according to one embodiment of the present invention, for use with assisted breathing or respiratory masks, such as continuous positive airway pressure ("CPAP") masks, auto adjusting positive airway pressure ("APAP") masks, dual positive airway pressure ("BiPAP") masks, and demand positive airway pressure ("DPAP") masks, and other mask types for oxygen, etc., to facilitate resting and sleep. The pillow 10 includes a pliable and resilient body 12, which can be formed of any suitable material, non-exhaustive examples of which include polymer foam, gel, fiber fill inside a casing, and fluid inside a bladder. The configuration of the pillow 10 may vary. In the embodiment illustrated in FIG. 1, the pillow 10 is generally rectangular in shape and includes a rear side 14, a front side 16, a first lateral side 18, and a second lateral side 20. Preferably but not necessarily, the pillow 10 has an axis of symmetry 22 extending between the rear side 14 and front side 16. The pillow 10 has a width W extending between the first lateral side 18 and the second lateral side 20 and a length L extending between the rear side 14 and the front side 16. The pillow 10 includes a head-supporting upper surface 30 and an opposite bottom surface 32. As illustrated in FIG. 7, the bottom surface is relatively planar. In another embodiment (not shown), the bottom surface 32 may optionally include a plurality of ridges.

The body 12 includes a first portion 40 and a second portion 42 that are preferably formed together as a unitary member. The first portion 40 and second portion 42 of the body 12 are preferably fabricated from the same material, such as foam, fiber fill, gel, etc., that provides good support and resiliency and, optionally, memory properties. The body 12 could also be a form-shaped bladder (not shown) inflated with air or liquid. The invention is not limited to any particular material making up the body 12.

Figure 2:
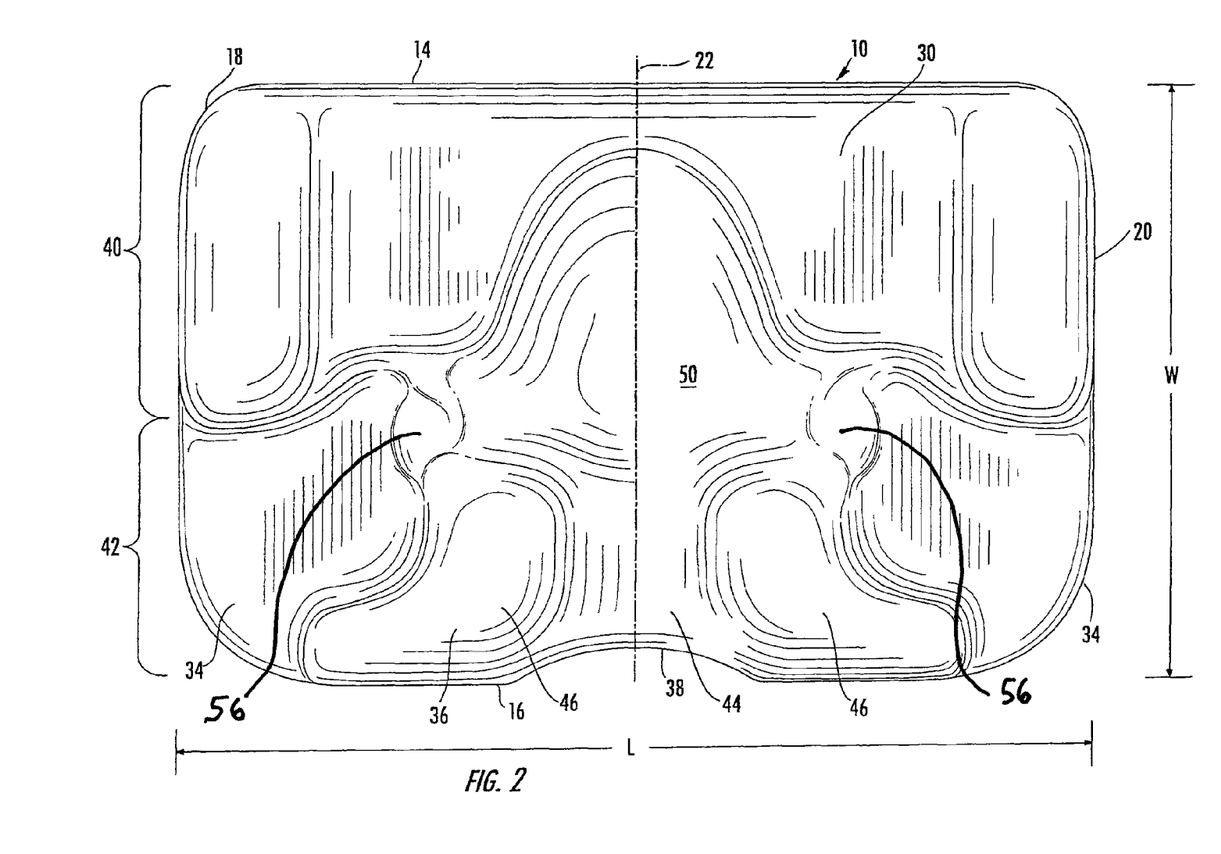
FIG. 2 is a top plan view illustrating the pillow of FIG. 1.
Figure 13:
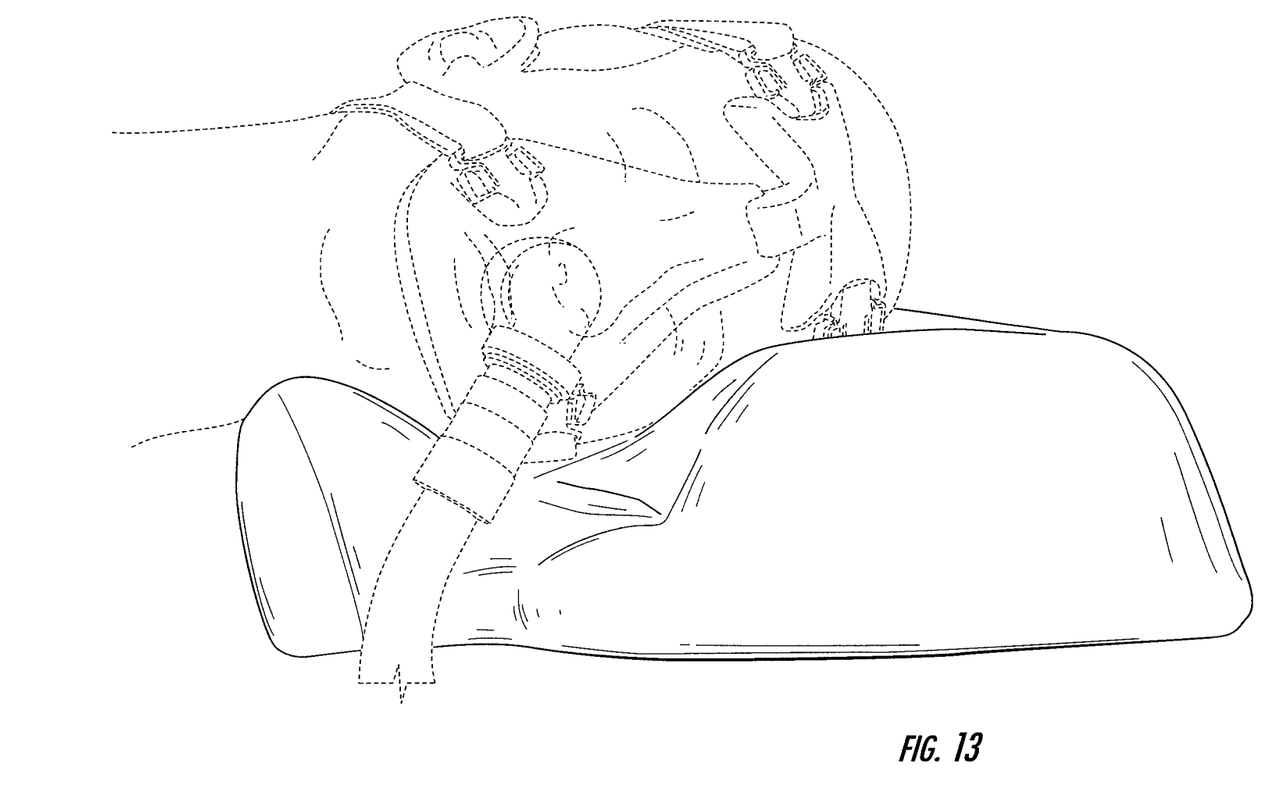
FIG. 13 shows a user wearing a respiratory mask and in a side-lying position with his/her head supported on the pillow of FIG. 1.

According to the embodiment illustrated in FIGS. 1-7, the first portion 40 and second portion 42 of the body 12 are generally rectangular in shape. The upper surface of the second body portion 42 includes a recess 34 adjacent to each of the first lateral side 18 and second lateral side 20 of the body 12 and a raised section 36 therebetween. Advantageously, as illustrated in FIG. 13, the recesses 34 provide pressure relief on the mask when the user of the pillow 10 is resting or sleeping on his/her side, so that the pillow will not exert any substantial degree of pressure on the mask and tubing for the mask. As illustrated in FIG. 2, one or both of the recesses 34 may extend into the first portion of the body 12. The recesses 34 are adjacent to pillow surfaces that comfortably support the user's head in the side-lying position, as further described below.

In one embodiment, as illustrated in FIG. 2, the second portion 42 of the body 12 can include an indentation 38 in the front side 16. This indentation 38 provides a curved area for the user's shoulder to rest for proper position and neck support when in the side-lying position.

Figure 3:
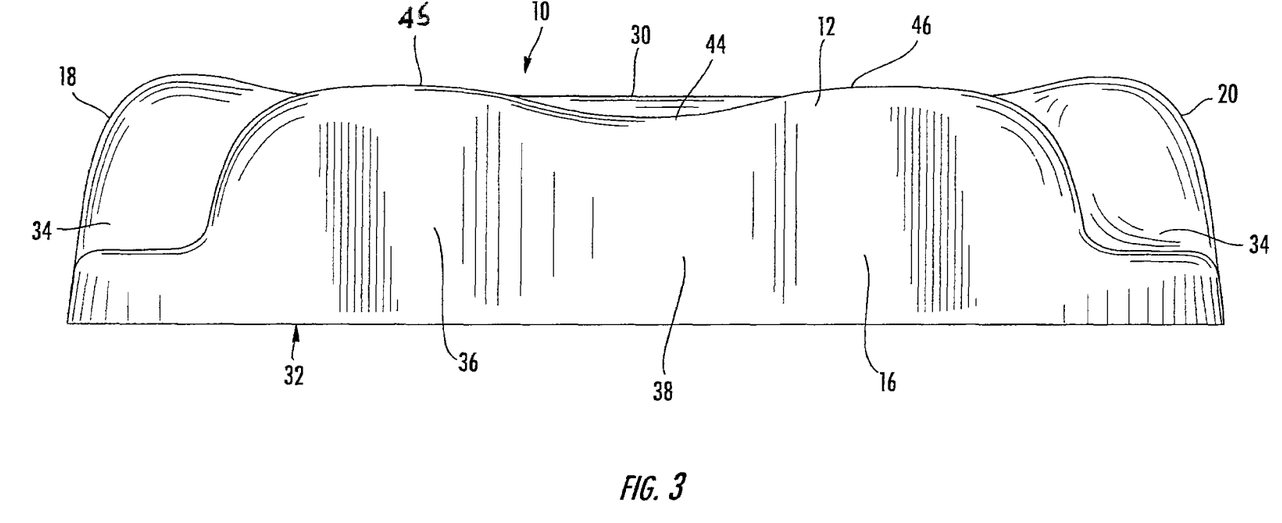
FIG. 3 is a front elevational view illustrating the pillow of FIG. 1.
Figure 4:
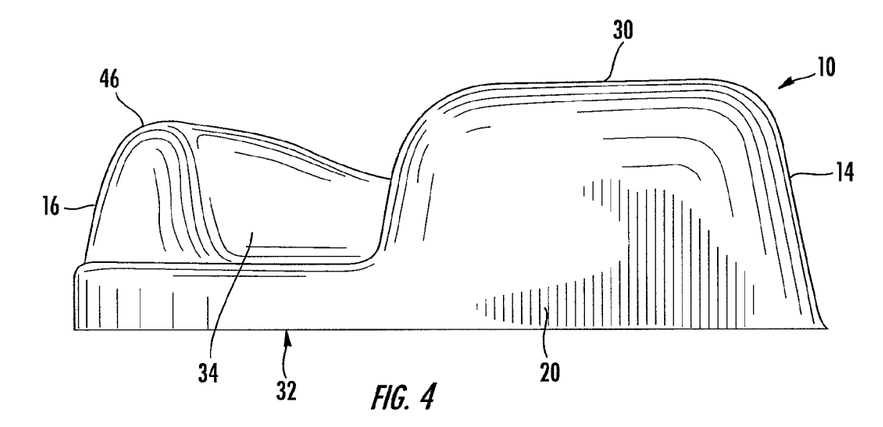
FIG. 4 is a right side view illustrating the pillow of FIG. 1.
Figure 5:
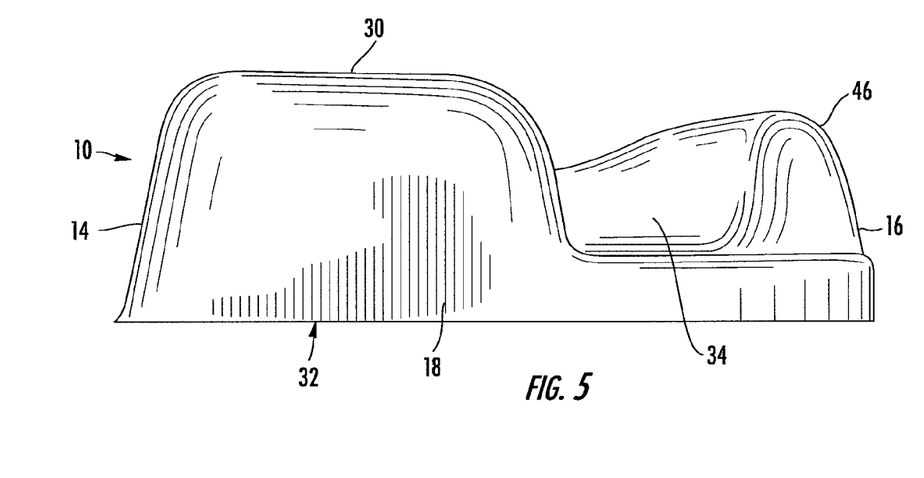
FIG. 5 is a left side view illustrating the pillow of FIG. 1.

The raised section 36 of the second portion 42 of the body 12 provides neck support for both back and side sleeping and resting. In one embodiment (not shown), the raised section 36 can include a bladder in which air or fluid can be added or released to adjust the elevation and amount of support provided. As illustrated in FIG. 3, the upper surface 30 of the raised section 36 may include an indentation 44 with raised areas 46 on each side of the indentation. Advantageously, the indentation 44 receives the user's neck and the raised areas 46 function to retain the user's neck within the indentation while the user is resting or sleeping.

In addition to recesses 34, as illustrated in FIGS. 1 and 2, the upper surface 30 of the body 12 may include a central indentation 50. The edge of the central indentation 50 in the first portion 40 of the body is curved and gently sloping to thereby provide a head support area for the user. As with the indentation 44 and raised areas 46 of the raised section 36, the central indentation 50 receives the user's head and the sloped side walls about the periphery of the central indentation function to retain the user's head within the central indentation while the user is resting or sleeping.

Figure 6:
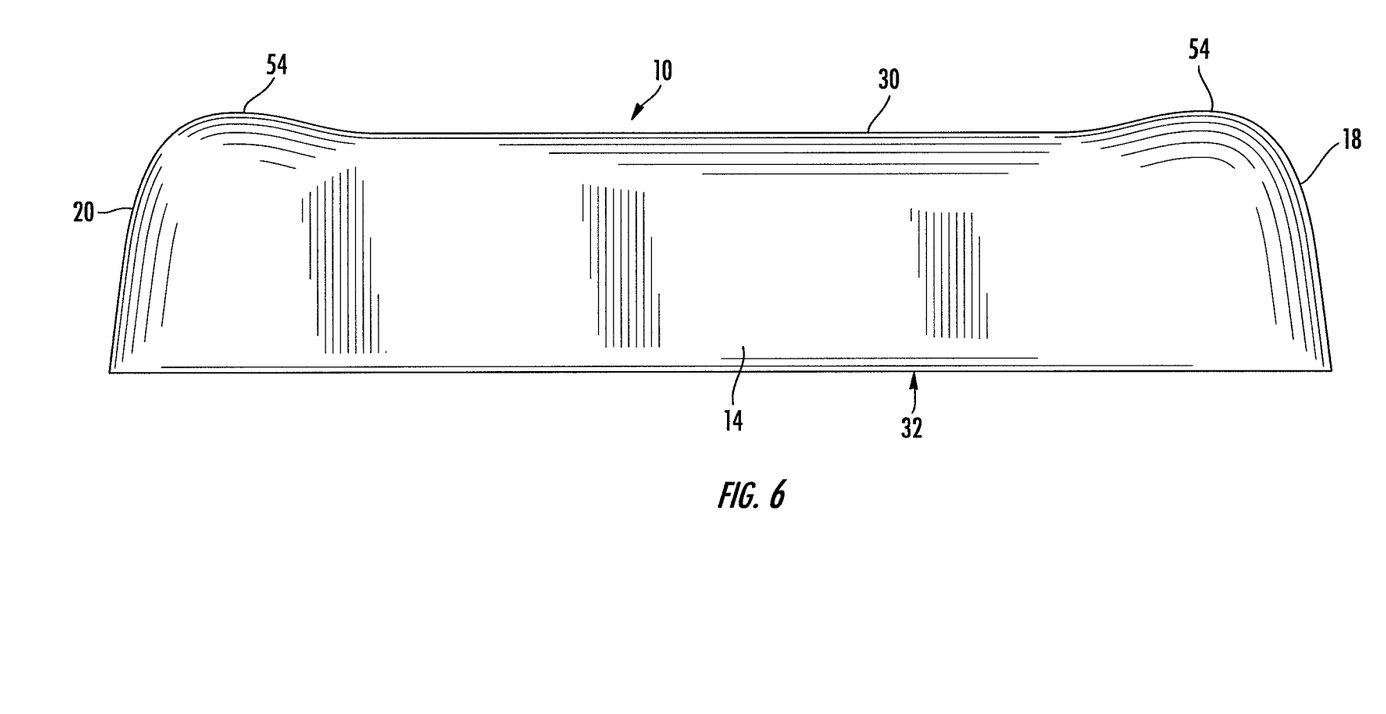
FIG. 6 is a rear elevational view illustrating the pillow of FIG. 1.

Referring to FIG. 6, the first portion 40 of the body 12 may include raised areas 54 adjacent to each of the first lateral side 18 and second lateral side 20. As illustrated in FIG. 13, the raised areas 54 provide support to the user's forehead when resting or sleeping in the side position to keep the user's head from rotating downward.

Referring to FIGS. 1 and 2, on either side of and adjacent to the indentation 44 and the central indentation 50, secondary recessed areas 56 may be provided. These secondary recessed areas 56 are for receiving either of the user's ears when in either of the left and right side-lying positions, to help relieve excess pressure on the ears and thereby improve overall comfort of the user.

In other embodiments (not shown), the pillow 10 can include other structure to accommodate or secure a hose for a respiratory mask. In one embodiment, the structure may include a routing channel or aperture formed into the pillow to reduce interference with the hose.

Typical materials of which the body 12 can be made (such as polymer foam, gel, fluid-filled bladders, etc.) may not be very comfortable if the skin is in direct contact with them, because they may not "breathe" very well. Accordingly, in preferred embodiments of the invention, a cover is provided for the pillow in order to enhance the comfort of the pillow. Referring to FIGS. 8-11, a fitted cover 60 for the pillow 10 is illustrated. It is important for the cover to substantially conform to the contours of the pillow, and in particular to the mask-receiving recesses 34, in order for the recesses to function properly to relieve pressure on the mask.

Figure 9:
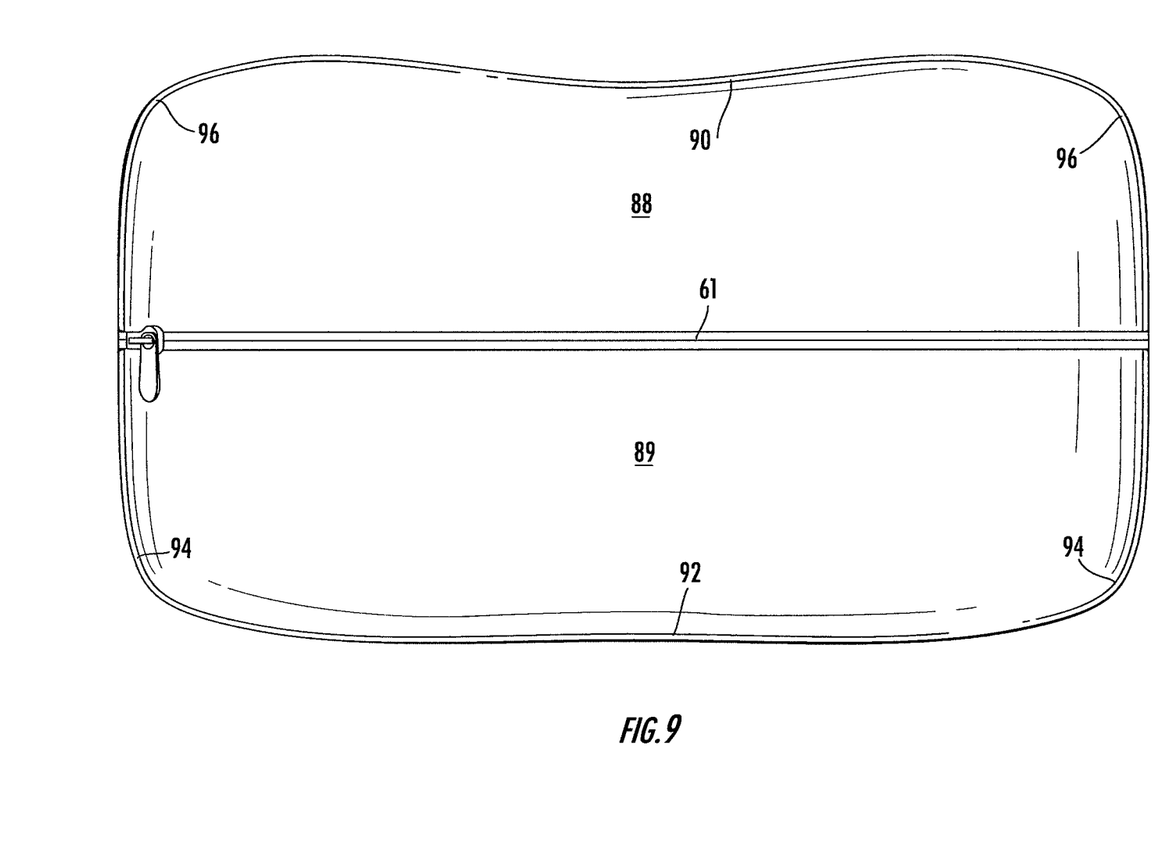
FIG. 9 is a bottom plan view illustrating the cover of FIG. 8.
Figure 10:
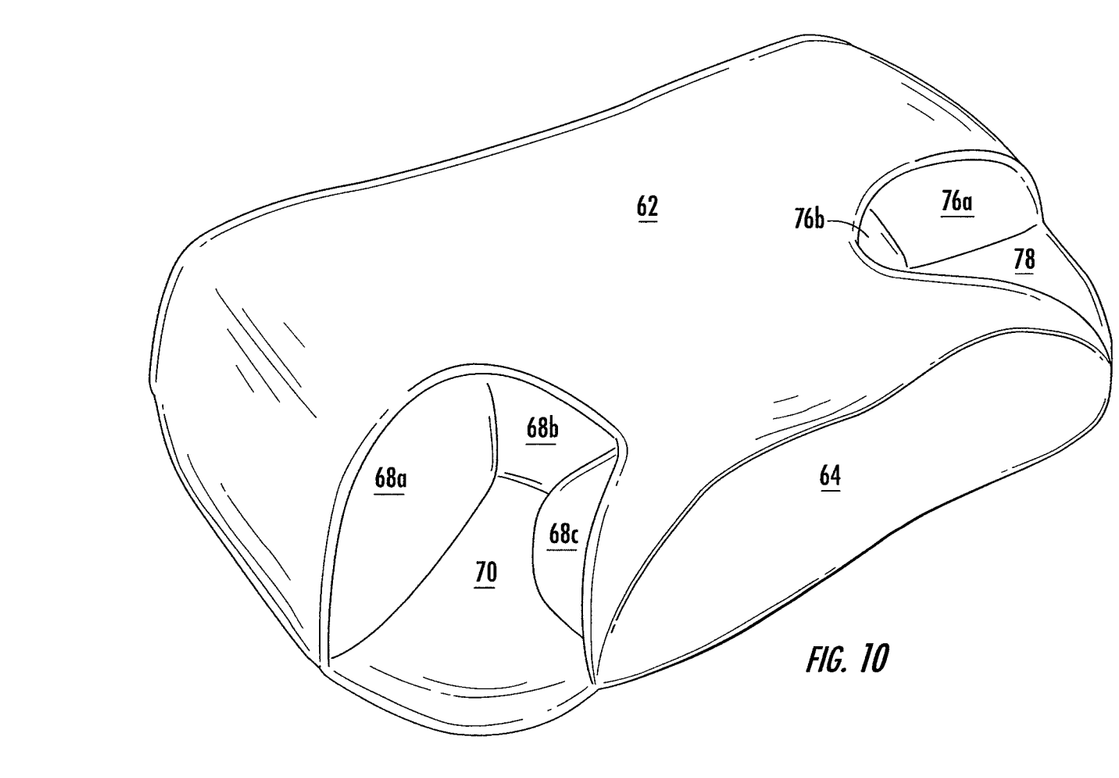
FIG. 10 is a perspective view illustrating the cover of FIG. 8.
Figure 11:
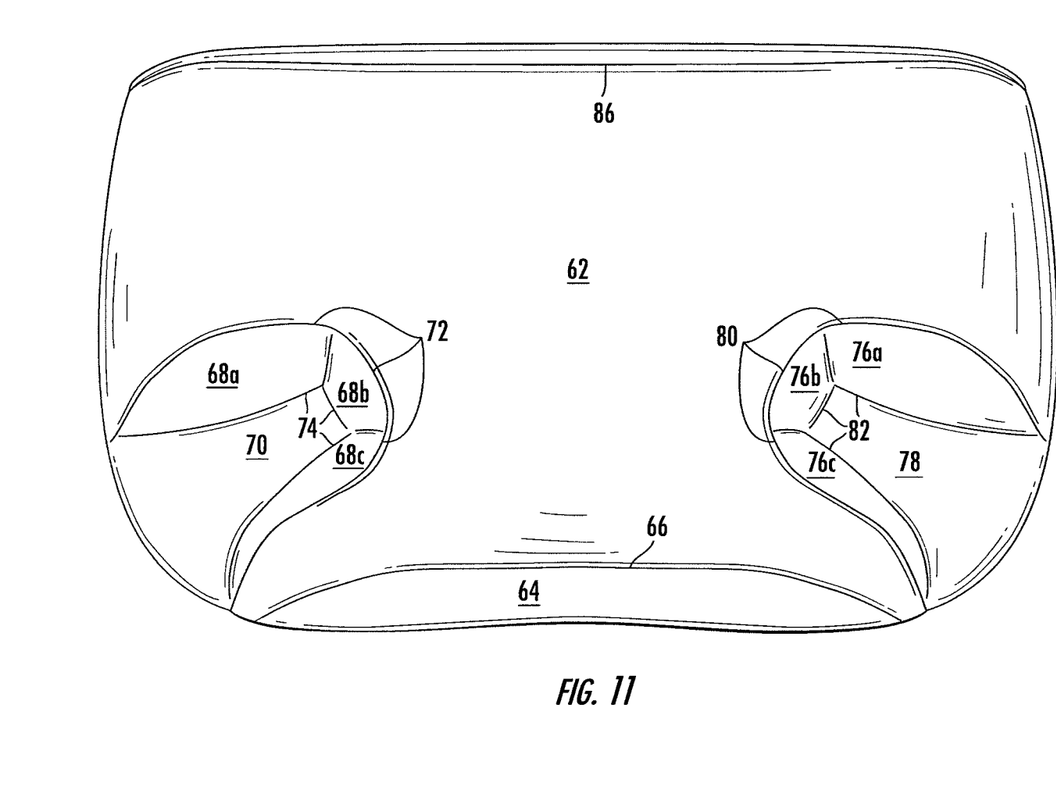
FIG. 11 is a top plan view illustrating the cover of FIG. 8.

As shown in FIG. 9, the fitted cover preferably includes an opening 61 on the bottom side of the cover corresponding to the bottom surface of the pillow, so that the pillow may be inserted into and removed from the cover to enable cleaning of the cover. As shown, a zipper is provided for closing the opening 61. As illustrated in FIGS. 8-11 and as discussed above, the cover is preferably fitted so that the cover substantially follows the contours and configurations of the pillow, and particularly those depressions, recesses, cavities, apertures, and/or raised portions that are structured to accommodate the mask or tubing for the mask. The cover 60 may also include structure to accommodate or secure a hose for the mask. In one embodiment (not shown), the structure of the cover may include one or more tethers to keep the hose from sliding or being positioned unfavorably. The cover can be sewn to fit the pillow. The cover may be made of a material that can be formed to fit the contours of the pillow by pressure, heat, or other means. Alternatively, instead of a separately made cover that is removable, the cover may comprise a material permanently applied to the surface of the pillow by any of various techniques, such as painting, dipping, or spraying. For example, flocking may be sprayed onto the pillow and adhered thereto by a suitable adhesive material.

In a preferred embodiment as shown in FIGS. 8-11, the cover 60 is a fitted cover made from pieces of fabric sewn together. More particularly, a first fabric piece 62 is sized and shaped to cover the majority of the upper surface of the pillow except for the recesses that receive the mask. The first fabric piece also drapes down over the opposite lateral sides of the pillow (except in the regions of the recesses). A second fabric piece 64 is sized and shaped to cover the front side and is sewn to the first fabric piece along a seam 66. Third, fourth, and fifth fabric pieces 68a, 68b, 68c are sized and shaped to cover the steeply sloped walls of the left-hand recess of the pillow, and a sixth fabric piece 70 is sized and shaped to cover the bottom wall of that recess. The fabric pieces 68a-c are sewn to the first fabric piece 62 along seams 72. The sixth fabric piece 70 is sewn to the fabric pieces 68a-c along seams 74.

Seventh, eighth, and ninth fabric pieces 76a, 76b, 76c are sized and shaped to cover the steeply sloped walls of the right-hand recess of the pillow, and a tenth fabric piece 78 is sized and shaped to cover the bottom wall of that recess. The fabric pieces 76a-c are sewn to the first fabric piece 62 along seams 80. The fabric pieces 76a-c are sewn to the tenth fabric piece 78 along seams 82. An eleventh fabric piece 84 (FIG. 8) is sized and shaped to cover the rear side of the pillow and is sewn to the first fabric piece 62 along a seam 86. Finally, twelfth and thirteenth fabric pieces 88, 89 (FIG. 9) are sized and shaped to cover the bottom surface of the pillow and are sewn to the eleventh fabric piece 84 along a seam 90, to the second fabric piece 64 along a seam 92, to the opposite edges of the first fabric piece 62 along seams 94, and to the sixth and tenth fabric pieces 70, 78 along seams 96.

Various types of fabric (woven, knitted, non-woven, etc.) made from various fiber types (natural, synthetic, natural/synthetic blends, etc.) can be used to make the sewn cover 60. In one embodiment, quilted woven fabric is employed for part of the cover and knitted fabric is employed for the rest. More particularly, in one embodiment, fabric pieces 62, 84, 88, and 89 are knitted fabric, with velour being particularly preferred. Fabric pieces 64, 68a-c, 70, 76a-c, and 78 are quilted woven fabric.

Figure 12:
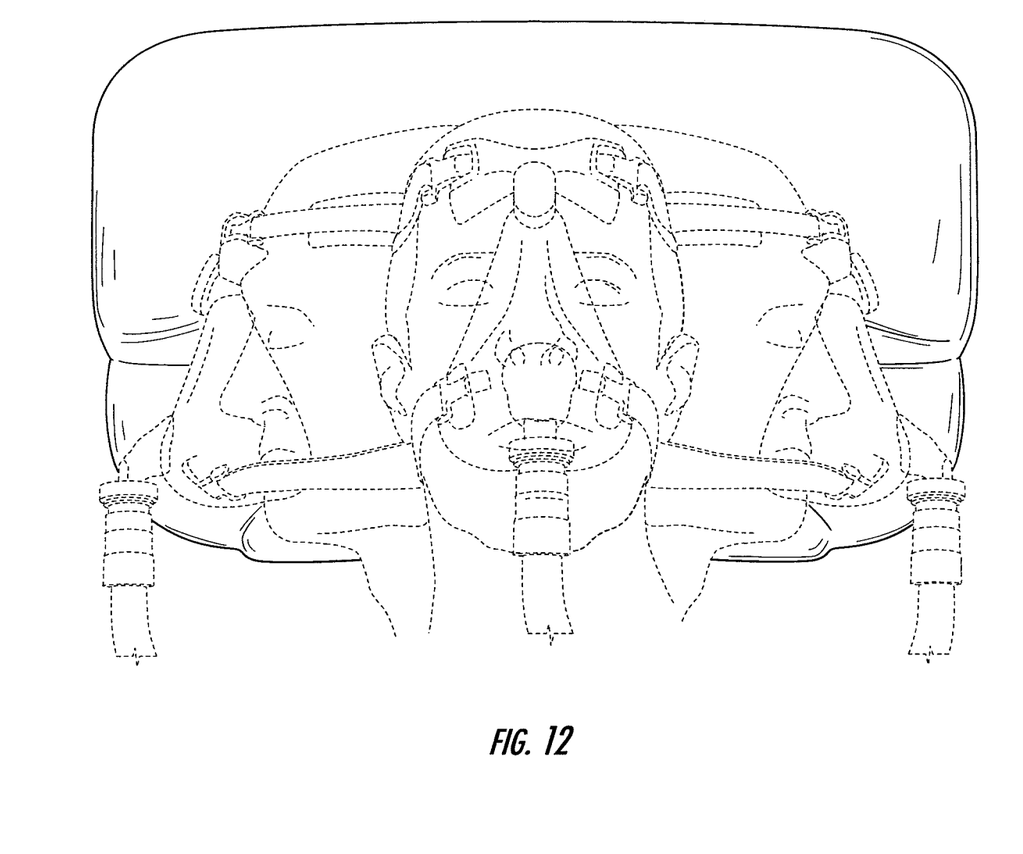
FIG. 12 shows a user wearing a respiratory mask and in a back-lying position with his/her head supported on the pillow of FIG. 1.

Referring to FIGS. 12 and 13, the pillow 10 is shown in use in the side- and back-lying positions. The pillow of the present invention may also be used in the stomach sleeping and resting positions. Advantageously, the cover of the pillow substantially follows the contours of the pillow and provides the user with contact-free use of a respiratory mask and the ability to easily sanitize the pillow after use. According to one embodiment, the pillow is used by positioning a cover on the pillow such that the cover substantially follows the contours and configurations of the pillow. A respiratory mask is positioned on the user's head. The user is positioned so that the user's shoulder is received in the lateral indentation 38 formed in the front side 16 of the second portion 42 of the pillow. The user's neck is positioned within the indentation 44 formed in the raised section 36 of the second portion 42 of the pillow. The user's head is positioned within the central indentation 50 formed in the first portion 40 of the pillow. In one embodiment, the positioning of the user's head comprises positioning the user's head so that it is facing away from the pillow. In another embodiment, the positioning of the user's head comprises positioning the user's head so that the side of the user's head is in contact with the cover of the pillow. In one embodiment, the method includes positioning the mask or hose for the mask in one of the recesses 34 formed in the second portion 42 of the pillow so that the pillow does not exert substantial pressure on the mask or hose.

Thus, the pillow of the present invention has depressions, recesses, cavities, apertures, and/or raised portions to accommodate various respiratory masks, such as those used for nighttime respiratory therapy. The depressions, recesses, cavities, apertures, and/or raised portions relieve pressure against the mask and the hoses or tubing supplying the mask when side sleeping or stomach sleeping. Since pressure against the mask can impede the performance and comfort of the mask, cause the mask seal to separate from the face and result in air leakage (which can cause irritation from the eyes drying out), and/or cause the mask to press uncomfortably against the user's face, the pillow and cover of the present invention and method of using the same eliminate many of the impediments to the user resting or sleeping while using a respiratory mask. Advantageously, the pillow and cover of the present invention allow the user to move and sleep in multiple positions—left side, right side, back, and stomach—while minimizing the pressure that is exerted on the respiratory mask.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device for use with a respiratory mask comprising a mask affixed to a user's face and a hose extending therefrom, the device comprising:
a pillow having a head-supporting upper surface defining at least one recess structured to receive the mask when the user is in a side-lying position so as to substantially prevent pressure from being exerted on the mask by the pillow; the pillow further comprising a routing aperture structured to receive and secure the hose extending from the respiratory mask to reduce interference with the hose; and a cover that at least partially covers the exterior surface of the pillow and substantially follows the contours of the at least one recess.

2. The device of claim 1, wherein the pillow is generally rectangular in shape and includes a rear side, a front side, a first lateral side, a second lateral side, a bottom surface, and the upper surface, the upper surface of the pillow defining two said recesses respectively adjacent to each of the first lateral side and second lateral side and a raised section therebetween, the recesses being configured and positioned to receive the mask when the user is lying either on the left side or the right side.

3. The device of claim 2, wherein the pillow further defines an indentation in the front side to accommodate the user's shoulder for proper position and neck support when in the side-lying position.

4. The device of claim 2, wherein the upper surface of the raised section defines an indentation with raised areas on each side of the indentation, the indentation being configured to receive the user's neck and the raised areas being configured to retain the user's neck within the indentation.

5. The device of claim 2, wherein the upper surface of the pillow defines a central indentation configured to provide a head support area for the user, the pillow having sloped side walls about a periphery of the central indentation that function to retain the user's head within the central indentation.

6. The device of claim 5, wherein the upper surface of the pillow defines secondary recessed areas on either side of and adjacent to the central indentation, the secondary recessed areas being configured for receiving either of the user's ears when in either of the left and right side-lying positions, to help relieve excess pressure on the ear and thereby improve overall comfort of the user.

7. The device of claim 2, wherein the upper surface of the pillow proximate to the rear side defines raised areas adjacent to each of the first lateral side and second lateral side, the raised areas being configured to provide support to the user's forehead when in the side-lying position to keep the user's head from rotating downward.

8. The device of claim 2, wherein the cover comprises multiple fabric pieces sewn together in a fashion to substantially conform the cover to at least the recesses and raised section.

9. The device of claim 8, wherein one fabric piece covers a majority of the upper surface of the pillow and separate fabric pieces cover the recesses that accommodate the mask.

10. The device of claim 9, wherein the one fabric piece is a knitted fabric and the separate fabric pieces for the recesses are quilted woven fabric.

11. The device of claim 1, wherein the cover is removable from the pillow and includes an opening into which the pillow is insertable and through which the pillow is removable.

12. The device of claim 1, wherein the routing aperture comprising a channel formed into the pillow.

13. The device of claim 1, wherein the cover comprises at least one tether structured to further secure the hose of the respiratory mask relative to the routing aperture.

14. A method of using a respiratory mask comprising a mask affixed to a user's face and a hose extending therefrom, the method comprising:
providing a pillow having a head-supporting upper surface that defines at least one recess configured to receive the mask when a user is in a side-lying position, the pillow further comprising a routing aperture structured to receive and secure the hose extending from the respiratory mask to reduce interference with the hose;
positioning a cover on the pillow so that the cover substantially follows the contours of the at least one recess;
positioning a respiratory mask on the head of a user;
positioning at least a portion of the hose of the respiratory mask in the routing aperture; and supporting the user's head on the cover and pillow such that the mask is received in the at least one recess so that the pillow and cover do not exert substantial pressure on the mask.

15. The method of claim 14, wherein the pillow is provided to be generally rectangular in shape and to include a rear side, a front side, a first lateral side, a second lateral side, an upper surface, and a bottom surface, the upper surface of the pillow defining two said recesses respectively adjacent to each of the first lateral side and second lateral side and a raised section therebetween, and wherein the supporting step includes the mask being received in one of the recesses when the user is lying on the left side and the mask being received in the other recess when the user is lying on the right side.

16. The method of claim 14, wherein the routing aperture comprising a channel formed into the pillow.

17. The method of claim 14, wherein the cover comprises at least one tether structured, and wherein the method comprises securing the tether to the hose of the respiratory mask to further secure the hose of the respiratory mask relative to the routing aperture.

* * * * *